United States Patent [19]

Dhawan

[11] Patent Number: 5,146,923
[45] Date of Patent: Sep. 15, 1992

[54] APPARATUS AND METHOD FOR SKIN LESION EXAMINATION

[76] Inventor: Atam P. Dhawan, 8085 Pine Terrace Dr., Cincinnati, Ohio 45255

[21] Appl. No.: 426,111

[22] Filed: Oct. 24, 1989

Related U.S. Application Data

[63] Continuation-in-part of Ser. No. 943,089, Dec. 18, 1986, abandoned.

[51] Int. Cl.⁵ .............................................. A61B 5/00
[52] U.S. Cl. .................................. 128/633; 128/664; 128/665
[58] Field of Search ............... 128/633, 634, 664, 665, 128/630; 606/9

[56] References Cited

U.S. PATENT DOCUMENTS

| | | | |
|---|---|---|---|
| 3,769,463 | 11/1973 | Goldman | 128/665 |
| 3,906,241 | 9/1975 | Thompson | 128/665 |
| 4,194,217 | 3/1980 | van den Bosch | 128/633 |
| 4,515,165 | 5/1985 | Carroll | 128/665 |
| 4,528,486 | 7/1985 | Arundel et al. | 128/665 |
| 4,570,638 | 2/1986 | Stoddart et al. | 128/665 |
| 4,600,011 | 7/1986 | Watmough | 128/665 |
| 4,616,657 | 10/1986 | Stoller | 128/665 |
| 4,693,255 | 9/1987 | Beall | 128/665 |
| 4,773,097 | 9/1988 | Suzaki et al. | 128/665 |

OTHER PUBLICATIONS

"Enhancement of Mammnographic Features by Optimal Adaptive Neighborhood Image Processing", by Dhawan; IEEE Trans. on Med. Imag; vol. 1M-5, No. 1, Mar. 1986, pp. 8-17.
"A Possible New Tool For Clinical Diagnosis of Melanoma: The Computer", by Cascinelli et al.; J. Am. Acad. of Derm.; vol. 16, No. 2, Part 1; Feb. 1987; pp. 361-367.
"Early Detection of Cutaneous Malignant Melanoma by Three-Dimensional Nevoscopy", by Dhawan; Computer Methods & Programs in Biomedicine; 21; (1985), pp. 59-68.
"Nevoscopy: Three-Dimensional Computed Tomography of Nevi & Melanomas In Situ by Transillumination", by Dhawan et al.; IEEE Trans. on Med. Imaging, vol. MI-3; No. 2; Jun. 1984, pp. 54-61.
"A Tutorial On ART (Algebraic Reconstruction Techniques)", IEEE Transactions, Nuclear Science NS-21, pp. 78-95, 1974, by Gordon.
"Computed Tomography by Transillumination to Detect Early Melanoma", IEEE Frontiers of Engineering and Computing in Health Care (1984) pp. 518-522, by Atam P. Dhawan, et al.
"Image Restoration by Weiner Deconvolution in Limited-View Computed Tomography", Applied Optics, vol. 24, No. 23, pp. 4013-4019, Dec. 1985, by Atam P. Dhawan, et al.
"Imaging Mammalian Tissues and Organx Using Laser Collimated Transillumination", J. Biomed, Eng. 1984, vol. 6, Jan., pp. 70-74, G. Jarry, et al.

*Primary Examiner*—David M. Shay
*Attorney, Agent, or Firm*—Arnold, White & Durkee

[57] ABSTRACT

This invention relates to an apparatus and method for skin lesion examination. The apparatus, a portable nevoscope, provides a hand-held device for viewing a skin lesion in situ in the presence of a uniform light distribution. The method of examining the skin lesion comprises the use of computer-based imaging to process a digitized image of the skin lesion and an expert system to analyze the image and diagnose the lesion.

33 Claims, 3 Drawing Sheets

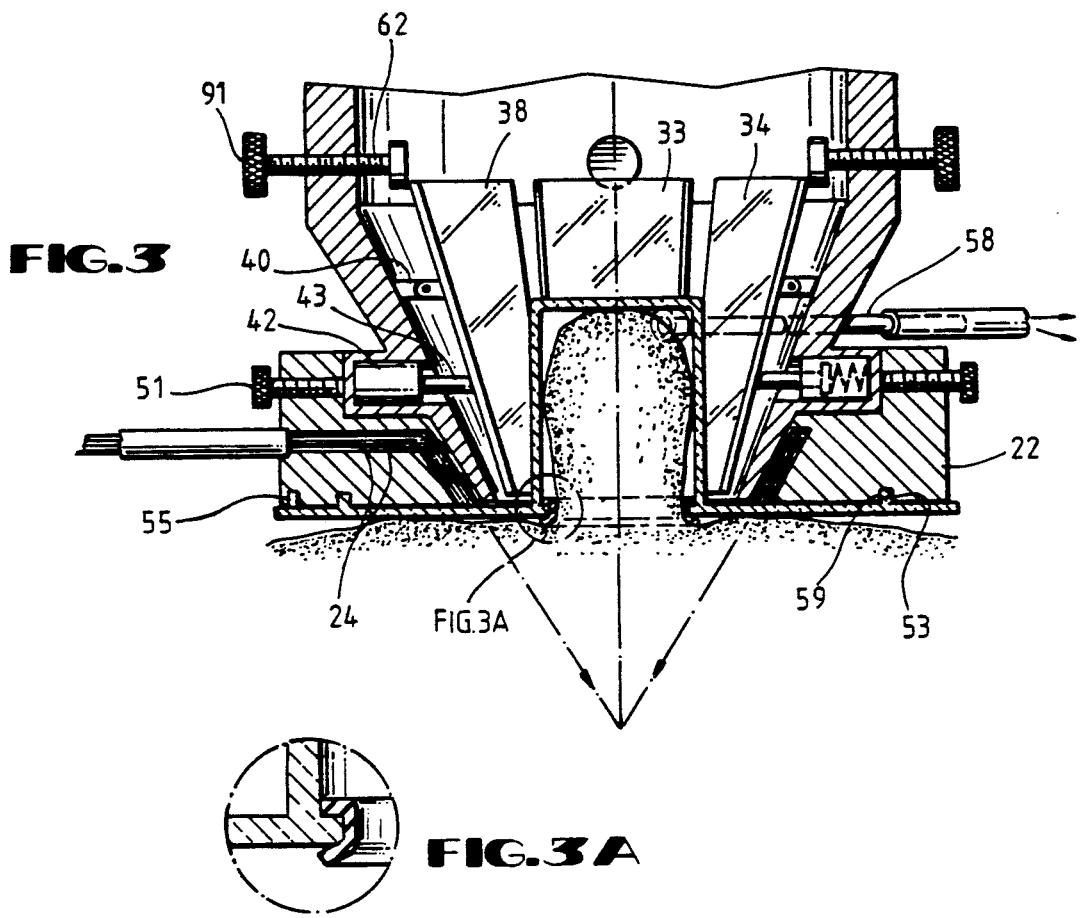
FIG. 3
FIG. 3A
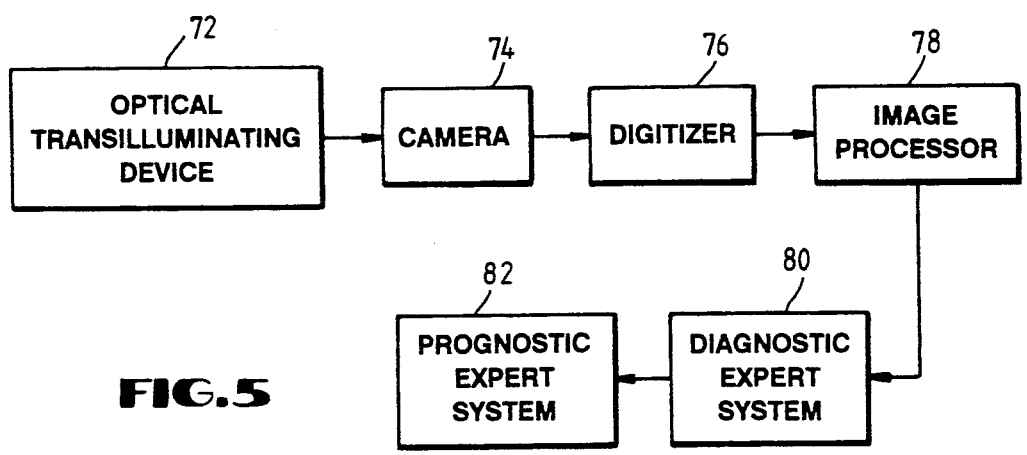
FIG. 5

APPARATUS AND METHOD FOR SKIN LESION EXAMINATION

BACKGROUND OF THE INVENTION

This application is a continuation-in-part of Application Ser. No. 943,089, filed Dec. 18, 1986 now abandoned. Applicant claims the benefit of said application for all purposes pursuant to 37 C.F.R. 1.78.

1. FIELD OF THE INVENTION

The present invention relates to an improved apparatus and method for identifying and characterizing skin specimens, such as nevi and lesions. The invention, more particularly, concerns a portable nevoscope which provides improved transillumination of an area of the skin, as well as sharply focused, simultaneous viewing of the entire circumference of the area. The invention also, more particularly, comprises a method of obtaining data from an area of the skin for subsequent processing to a form suitable for analysis, diagnosis, and prognosis.

2. DESCRIPTION OF THE PRIOR ART

A nevoscope is a device used to examine the skin in situ for lesions, nevi and the like. The nevoscope, among other things, provides a noninvasive means for measuring nevi thickness.

The nevoscope of the prior art is designed to be used in conjunction with a stereomicroscope, such as the Model M8 manufactured by Wild Corporation. The nevoscope in that instance comprises a vertically disposed plastic cylinder mounted around the objective lens of a stereomicroscope. The nevoscope is described in the article, "Nevoscopy: Three-Dimensional Computed Tomography of Nevi and Melanomas In Situ by Transillumination," IEEE Transactions on Medical Imaging, Vol. MI-3, No. 2, Jun. 1984 by Atam P. Dhawan, Richard Gordon, and Rangaraj M. Rangayyan.

The conventional nevoscope is focused by loosening a nylon screw on a plastic cylinder and moving the plastic cylinder axially along the tube of the objective lens of a stereomicroscope. When proper focus is obtained, the nylon screw is then tightened to hold the plastic cylinder firmly in position on the stereomicroscope. This method of focusing, however, is clumsy and ill-suited to fine focusing adjustments.

A laterally disposed plastic plate with a central slot screws into the bottom of the plastic cylinder of the conventional nevoscope. The center slot is rectangular in the plane of the plastic plate and trapezoidal in its cross-sectional shape. One side of the trapezoid forms an angle of 22.5 degrees with the vertical axis of the cylinder; the other side forms an angle of 45 degrees. Two front surface mirrors are glued onto the slated inner sides or walls of the central slot and thereby are at angles of 45 degrees and 22.5 degrees from the vertical. Unfortunately, the optical versatility of this mirror arrangement is limited in that the angle of the mirrors cannot be adjusted, and the mirrors cannot be rotated to provide a 360 degree viewing range of the skin area of interest.

The conventional nevoscope is illuminated by two fiber optic bundles which are inserted in holes drilled at 45 degree angles in opposite sides of the plastic cylinder and plate. This lighting arrangement unfortunately provides transillumination of poor quality due to the nonuniformity of the light distribution in the region of the skin lesion.

It has been found that the clarity and focus of the image provided by a nevoscope is affected by the mechanical coupling of the bottom surface of the nevoscope with the skin area of interest. Ideally, the bottom surface of the nevoscope should be flush with the skin throughout its 360 degrees of contact. As a practical matter, this ideal arrangement has been frequently unattainable due to skin surface topography in many areas of diagnostic interest.

The prior art nevoscope is large and nonportable, making it impossible to use in practical clinical applications. The various body locations where skin lesions are present necessitate the need for a nevoscope in clinical applications that is much smaller than the nevoscope of the prior art.

Images obtained from the prior art nevoscope have been digitized and analyzed to determine lesion thickness. This analysis has included obtaining two-dimensional vertical sections and three-dimensional reconstruction of skin lesions using reconstruction methods well known in the art, such as algebraic reconstruction techniques and geometric deconvolution. These algebraic reconstruction techniques are discussed in publications such as "A Tutorial on ART (Algebraic Reconstruction Techniques)", IEEE Transactions, Nucl. Science NS-21, pp. 78–95, 1974, by Gordon and "Image Reconstruction by Wiener Deconvolution in Limited-View Computed Tomography", Applied Optics, Vol. 24, No. 23, pp. 4013–4019, Dec. 1985, by Dhawan, Rangayyan and Gordon. The thickness of the skin lesions has been obtained from the reconstruction of the two-dimensional vertical sections. Methods employed to calculate lesion thickness are discussed in, "Nevoscopy: Three-Dimensional Computed Tomography of Nevi and Melanomas In Situ by Transillumination supra, and in "Computed Tomography By Transillumination to Detect Early Melanoma," IEEE Frontiers of Engineering and Computing in Health Car (1984) pp. 518–522, by Atam P. Dhawan, Richard Gordon, and Rangaraj M. Rangayyan.

SUMMARY OF THE INVENTION

The present invention provides a portable means for examining, analyzing, and diagnosing a skin lesion. The apparatus embodiment of this invention comprises a portable nevoscope which provides a noninvasive means to examine a skin lesion in situ. The method embodiment of this invention provides a means to process and analyze skin lesion data relating to properties such as thickness, color, size, pigmentation, boundary, and texture. Once these lesion characteristics are determined, they can be compared to skin lesion data contained in a knowledge-based system and analyzed. The diagnosed skin lesion may also be evaluated in light of medical histories contained in a knowledge-based system to obtain a prognosis of the skin lesion.

In a broad sense, the present invention comprises a system in which a specimen of skin, containing a lesion, is more or less isolated in situ or in vivo by lifting or stretching the specimen away from the remaining skin. The specimen is then transilluminated uniformly around its entire periphery. Preferably, the light is directed into the skin surrounding the specimen at an angle of about 45 degrees, and the specimen is then illuminated from below by backscattered light from within the tissue underlying the specimen.

While the specimen is thus illuminated, images of the lesion are obtained at a plurality of viewing angles relative to an axis substantially central and normal to the specimen. The images are also sufficient in number to provide 360 degrees coverage of the specimen about such axis. A three-dimensional image of the specimen is then obtained by computerized axial tomography. A principal object of the invention is to detect and define nevi, including skin lesions.

The apparatus embodiment of the present invention in a broad aspect is a portable nevoscope. The portable nevoscope comprises a cylindrical lens housing, a lesion or specimen housing, a plurality of adjustable mirrors, means for uniformly transilluminating the skin lesion, and means for focusing the image of the skin lesion viewed through the nevoscope. The nevoscope also preferably includes means for effecting a suction coupling of a skin lesion to the nevoscope. The lens housing preferably includes an eyepiece for improved viewing.

The plurality of mirrors is preferably mounted within a separate mirror housing near the wall of the mirror housing. The mirrors are oriented such that they reflect toward the center of the mirror housing.

The suction coupling capabilities of the new nevoscope enable the bottom surface of the nevoscope to be flush with the skin throughout 360 degrees of contact. This flush mating of the nevoscope and skin provides superior transillumination, thus allowing the nevoscope user to obtain a higher degree of clarity and focus. When the nevoscope user wishes to rotate the nevoscope about the skin specimen in order to obtain different views of the specimen, the suction coupling is merely released and the nevoscope is then rotated.

In the preferred embodiment of the invention disclosed herein, rotation of the plurality of mirrors about the skin specimen may also be accomplished without having to release the suction coupling to the patient's skin. By releasing a locking mechanism, which locks the mirror and lens assembly to the specimen housing, rotation of the mirrors 360° about the specimen housing is possible.

In a preferred embodiment, a cup-like specimen housing is inserted in the lower end of the mirror housing to receive a skin specimen. The specimen housing is made of high quality, optically flat material, such as plastic or glass, which allows light to pass through it without any significant attenuation.

The base of the specimen housing is a horizontal planar surface which extends from the base of the vertical sides of the cup-like section of the specimen housing, radially outward to the edge of the mirror housing. This planar surface is a planar waveguide which is made from the same type of high quality, optically flat material as the rest of the specimen housing. An inlet tube with an attached squeeze bulb or other suction device is inserted into the specimen housing to provide the suction capabilities needed to draw the skin specimen into the skin chamber.

The present invention preferably employs fiber optic filaments which are positioned around the entire circumference of the skin lesion to provide uniform transillumination of the skin lesion. The filaments may be uniformly dispersed in an illuminator ring housing surrounding the lower portion of the lens housing and the specimen housing. The filaments are arranged such that a cone of light is directed downward into the skin surrounding the lesion at an angle of approximately 45 degrees.

An eyepiece cylinder is centrally and slidably mounted in the top of the lens housing to provide ease of focus. In a preferred embodiment, the eyepiece cylinder contains two lenses, one mounted near the top of the cylinder and one mounted near the bottom of the cylinder, for enhanced optical performance. The lens housing also contains a lens whose axial position can be easily adjusted, as by the use of a knob on the outside of the lens cylinder. Preferably, the lens housing contains a second lens, mounted above the adjustable position lens, for enhanced optical performance. These two means of lens adjustment enable the nevoscope user to make fine focusing adjustments with a minimal degree of manual effort.

In addition to the light filaments and waveguides, a light element is adjustably mounted in the side of the lens housing to provide surface illumination of the skin specimen. The orientation of the light element can be varied to change the angle at which light is directed or aimed toward the specimen. In a preferred embodiment, the light element has an adjustable intensity to control light brightness.

The image seen through the nevoscope of the present invention can be further controlled by adjusting the opening in an entrance pupil mounted in the lens housing between the lens and the mirror housing. The entrance pupil opening can be adjusted by mechanical shutter control means well known in the optical art. A focus correcting plate containing regions with different refractive indices may be mounted in the mirror housing below the entrance pupil to provide a focused image of the multiple views of the skin lesion produced by the multiple mirrors. Alternatively, if the lenses mounted in the lens housing can provide a depth of focus sufficient to simultaneously focus all images seen through the nevoscope, the focus correcting plate is unnecessary. In a preferred embodiment, a depth of focus of 3–6 millimeters is sufficient to alleviate the need for a focus correcting plate.

The present invention is compatible with a video or still photography camera. The images recorded by such camera equipment can be digitized and processed in order to analyze the skin lesion. A digitized image of a skin lesion can be analyzed and diagnosed using the method of the present invention. This method includes taking separate pictures of the skin lesion with an optical device equipped with a color filter. Such a picture will produce a color component image. Color component images are taken with red, blue, and green filters in the method of the present invention. Alternatively, red, green, and blue components of the color image can be directly obtained using a color camera with an RGB (red, green, and blue) decoder, such as a 3 chip color camera manufactured by Sony Corporation.

The method of the present invention includes reconstructing a three-dimensional, digital image of the skin lesion from computed skin lesion projections using ART and deconvolution methods well known in the art. Publications which describe ART and deconvolution methods suitable for reconstructing a three-dimensional digital image are "A Tutorial on ART (Algebraic Reconstruction Techniques)", IEEE Transactions, Nucl. Science NS-21, pp. 78–95, 1974, by Gordon and "Image Reconstruction by Wiener Deconvolution in Limited-View Computed Tomography", Applied Optics, Vol. 24, No. 23, pp. 4013–4019, Dec. 1985, by Dhawan, Rangayyan and Gordon.

These methods involve digitizing the color component images obtained with a nevoscope and storing the digitized images in a computer memory. The digitized image is stored as a matrix of points or pixels. Each matrix element or pixel is denoted by an x-y coordinate designation. The gray scale value at each pixel is denoted by g(x,y). The projection data is then computed from the stored images. The images are then registered in proper orientation and scanned for a selected cross-section. Gray scale values along cross-section lines are read from the image files. These gray scale values form the one-dimensional projection data which is used to reconstruct an initial two-dimensional cross-section of the skin lesion using Algebraic Reconstruction Techniques (ART). The ART method of image reconstruction updates the gray scale values at each pixel, g(x,y), iteratively to match the projection data.

Next, the point spread function of the reconstruction process is obtained using the following steps. First, a point image is simulated by assigning a non-zero high gray scale value to a pixel centrally located in a two-dimensional pixel matrix. All pixels in the matrix other than the central pixel are assigned low gray scale values. A gray scale value of 255 is illustrative of a suitable high gray scale value for the central pixel. A gray scale value of 20 is illustrative of suitable gray scale values for the remaining pixels. The gray scale value of each pixel in this matrix at point (x,y) is denoted by j(x,y).

Second, a projection axis $p(\Theta)$ is selected for the point image. Projection axis $p(\Theta)$ passes through the intersection of the x and y axes of the point-image at an angle $\Theta$ counterclockwise from the x axis. Alternatively, $p(\Theta)$, may be thought of as a counterclockwise rotation of the x axis by angle $\Theta$.

A group of n projection rays, each ray denoted by $r(n,\Theta)$ and perpendicular to projection axis $p(\Theta)$, is selected. The sum of all gray scale values, $Z(n,\Theta)$, of all pixels along each ray $r(n,\Theta)$ is then computed as follows:

$$Z(n,\Theta) = \sum_{\substack{\text{along} \\ r,(n,\Theta)}} j(x,y) \qquad (1)$$

This is done for all n projection rays made across the two-dimensional pixel matrix at a given angle $\Theta$. For each angle at which $Z(n,\Theta)$ values are obtained, an array, $A_z(\Theta)$ of all $Z(n,\Theta)$ values is stored. Each $A_z(\Theta)$ array contains a projection of the point image.

Third, the same ART method which was used to obtain a two-dimensional cross-section of the skin lesion is applied to the point image projections to obtain a reconstructed point image. The gray scale at coordinate (x,y) for each pixel in the reconstructed point image is denoted by k(x,y).

Fourth, the Fourier component of the point image, J(u,v), is determined by the equation:

$$J(u,v) = \frac{1}{(MN)} \sum_{x=0}^{M-1} \sum_{y=0}^{N-1} j(x,y) \exp\left[-j2\pi\left(\frac{ux}{M} + \frac{vy}{N}\right)\right] \qquad (2)$$

Fifth, the Fourier component of the reconstructed point image, K(u,v), is determined by the equation:

$$K(u,v) = \frac{1}{(MN)} \sum_{x=0}^{M-1} \sum_{y=0}^{N-1} k(x,y) \exp\left[-j2\pi\left(\frac{ux}{M} + \frac{vy}{N}\right)\right] \qquad (3)$$

In equations (2) and (3), u=0,1,2 ..., M−1 and v=0,1,2 ..., N−1, where M and N are the matrix dimensions Sixth, the Fourier component of the point spread function, H(u,v), is determined by the equation:

$$H(u,v) = [K(u,v)] / [J(u,v)] \qquad (4)$$

Seventh, the Fourier component of the initial reconstruction of the skin lesion, G(u,v), is determined by the equation:

$$G(u,v) = \frac{1}{(MN)} \sum_{x=0}^{M-1} \sum_{y=0}^{N-1} g(x,y) \exp\left[-j2\pi\left(\frac{ux}{M} + \frac{vy}{N}\right)\right] \qquad (5)$$

Eighth, a two-dimensional deconvolution is performed using the following equation:

$$F(u,v) = \frac{|H(u,v)|^2}{[|H(u,v)|^2 + W(u,v)]} \frac{G(u,v)}{H(u,v)} \qquad (6)$$

where W(u,v) is a model noise to signal ratio for the frequencies u and v used in the Fourier domain to compute the Fourier transforms shown in equations (2)–(6).

The final reconstruction of the skin lesion, f(x,y), is then determined by the equation:

$$f(x,y) = \sum_{u=0}^{M-1} \sum_{v=0}^{N-1} F(u,v) \exp\left[j2\pi\left(\frac{ux}{M} + \frac{vy}{N}\right)\right] \qquad (7)$$

The present invention employs an expansion algorithm to analyze gray scale data from the digitized skin lesion image in order to locate the skin lesion boundary.

The color component images of the skin lesion are analyzed using the method of the present invention in order to determine the color and texture characteristics of the skin lesion. The size and thickness of the skin lesion are determined from the pixel scale dimensions and the number of pixels encompassed by the lesion image.

The present invention employs a knowledge-based expert system to diagnose the skin lesion based upon the characteristics determined from the analysis. This invention further employs a knowledge-based expert system containing prognostic probabilistic models in order to obtain a prognosis of the skin lesion.

BRIEF DESCRIPTION OF THE DRAWINGS

FIG. 3 is an enlarged cross-sectional view of the mirrors housing and specimen housing.

FIG. 3a is an enlarged view of the specimen housing base.

FIG. 5 is a block diagram of the skin lesion image processing, analysis and diagnosis method.

DETAILED DESCRIPTION OF THE PREFERRED EMBODIMENT

Figure 1:
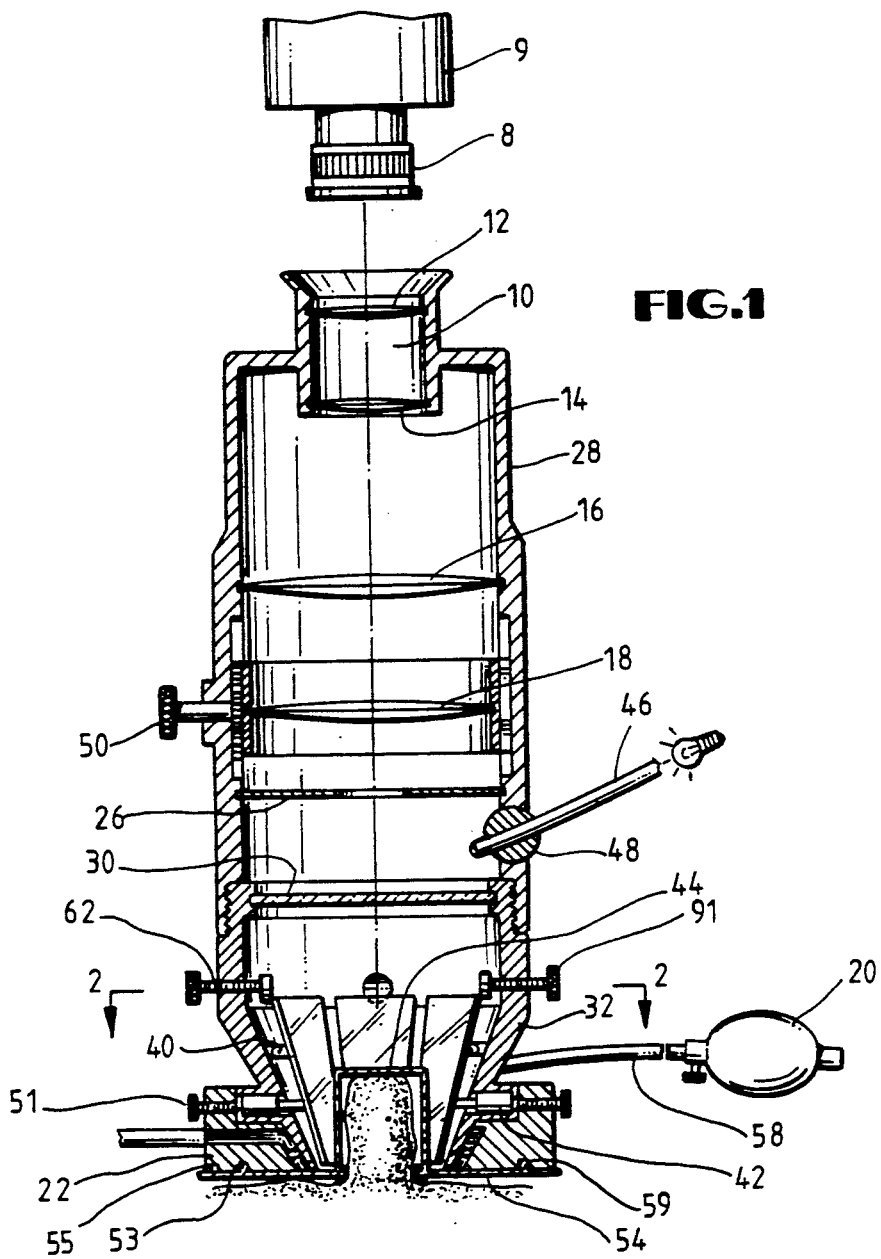
FIG. 1 is a cross-sectional full view of the nevoscope.
Figure 4:
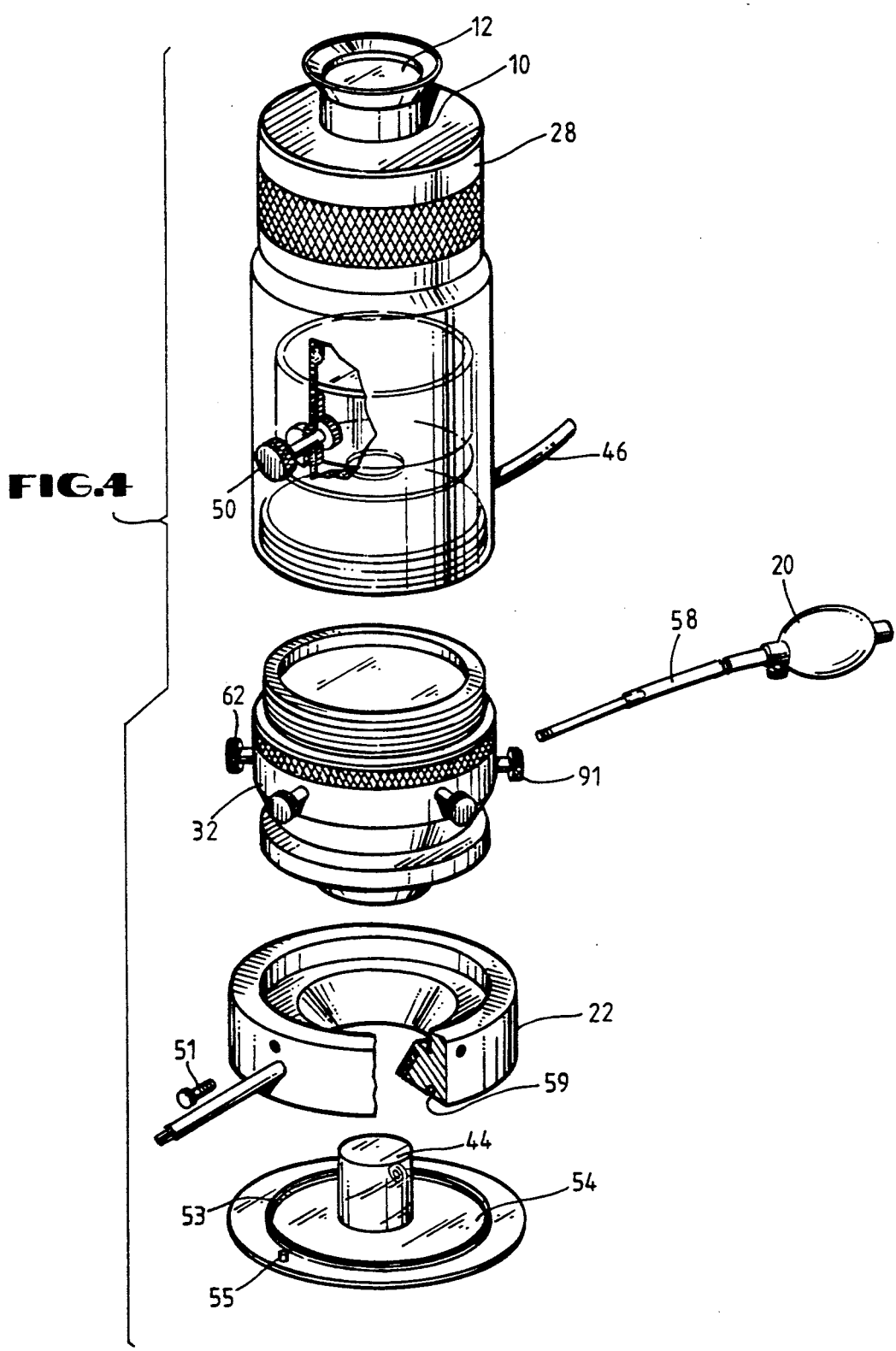
FIG. 4 is an exploded isometric view of the nevoscope.

Referring to FIGS. 1 and 4, a portable lens housing 28 forms the major structural component of the nevoscope. An eyepiece 10 is slidably inserted into the top center section of the lens housing 28. The eyepiece 10 contains an upper lens 12 and a lower lens 14. A camera 9 is positioned to record images viewed through eyepiece 10. Camera 9 may be a still or a video camera.

The lower section of lens housing 28 contains female threads which receive male threads on the upper portion of mirror housing 32. These threads provide a means for coupling the mirror housing 32 and lens housing 28 as well as a means to adjust the distance between the lenses 16 and 18 and the specimen. Other methods of mechanical coupling well known in the mechanical arts are suitable to couple lens housing 28 and mirror housing 32.

The central section of the lens housing 28 contains two lenses. The upper lens 16 is mounted in a fixed axial position. The lower lens 18 is equipped with a positioning mechanism 50 which provides a means of adjusting the axial position of the lower lens 18. This feature provides the nevoscope with fine focusing capabilities.

Directly below the lower lens 18, an entrance pupil 26 is mounted in the lens housing 28. This entrance pupil 26 is an aperture whose opening size can be adjusted by mechanical adjustment means well known in the optical art.

A light element 46 is adjustably mounted in the wall of the lens housing 28 below the entrance pupil 26. The light element 46 is directed to provide surface illumination to the skin lesion. The orientation of light element 46 can be varied. In a preferred embodiment, light element 46 extends through the center of a spherical ball joint 48 rotatably mounted in the side of lens housing 28. The rotational capability of ball joint 48 permits the nevoscope user to directionally aim the light element 46 on the skin lesion. In a preferred embodiment, the brightness of light emitted from light element 46 is adjustable.

A cylindrical mirror housing 32, containing six mirrors 33-38, is inserted in the lower section of the lens housing 28. In a preferred embodiment, the lower portion of mirror housing 32 converges radially inward in a conical configuration. A focus correction plate 30 is mounted in the top section of the mirror housing 32. This focus correcting plate 30 contains several regions of varying refractive indices to provide a focused image of the multiple views of the skin lesion produced by the multiple mirrors 33-38.

A specimen housing 44, resembling an inverted cup, is inserted in the bottom of the mirror housing 32. The base of the specimen housing 44 is a planar optical waveguide 54 extending from the bottom of the vertical side of the specimen housing 44 radially outward to the edge of the mirror housing 32. A lip or ridge 53, integrally formed with optical waveguide 54 is mounted on top of optical waveguide 54, centrally located between the outer edge of optical waveguide 54 and the vertical side of specimen housing 44. Lip 53 extends entirely around the vertical sides of specimen housing 44. Specimen housing 44, including optical waveguide 54, is made from high quality, optically flat material, such as plastic, which allows light to radiate through it without significant attenuation. A vertical alignment post 55 is mounted on top of optical waveguide 54 near the outer edge of optical waveguide 54.

As shown in FIG. 3, an inlet tube 58 is inserted in the vertical section of specimen housing 44. A squeeze bulb 20 is attached to the outer end of the inlet tube 58 to provide a means of producing suction on the specimen. The outer end of inlet tube 58 extends the side of mirror housing 32. In a preferred embodiment, as shown in FIG. 3a, the intersection of the vertical side of the specimen housing 44 and the optical waveguide 54 is coated with a gasket material 49 to improve the seal between the specimen housing 44 and the skin lesion when suction is applied on the specimen.

An illuminator ring 22 surrounds the lower section of the mirror housing 32. Illuminator ring 22 is fastened to mirror housing 32 by a thumbscrew 51 extending horizontally through illuminator ring 22. In a preferred embodiment, two thumbscrews 51 may be used to fasten illuminator ring 22 to mirror housing 32. The base of illuminator ring 22 contains a groove of sufficient size and placed at a radial location to receive lip 53 on optical waveguide 54. This lip and groove arrangement provides a means of centrally positioning specimen housing 44 within mirror housing 32 and mechanically coupling specimen housing 44 to illuminator ring 22. The base of illuminator ring 22 contains a female receptacle 59 positioned to receive alignment post 55 thereby preventing rotational movement between specimen housing 44 and illuminator ring 22. Fiber optic filaments 24 are uniformly dispersed in the illuminator ring 22 to extend around the specimen housing 44.

As shown in FIGS. 3 and 4, the mirror housing 32 is coupled to the illuminator ring 22 in such a fashion that the entire lens housing 28 with mirror housing 32 attached may be rotated with respect to the illuminator ring 22. Because of the vertical alignment post 55, rotation of the mirror housing 32 does not produce a corresponding rotation in thee illuminator ring 22, provided that locking thumb screws 51 are not set in their locket position locking the mirror housing 32 to the illuminator ring 22.

In a preferred embodiment, the outer wall of the illuminator ring 22 is vertical and the inner wall converges radially inward in a conical configuration at an angle matching that of the lower portion of mirror housing 32. The fiber optic filaments 24 are positioned in illuminator ring 22 such that their light is directed downward at a 45° angle through the bottom of the illuminator ring and through optical waveguide 54 and onto the area of skin surrounding the skin lesion to deliver uniform transillumination of the skin lesion. The light which penetrates the skin in a 45° cone and is backscattered up through the lesion to provides the transillumination.

The ring of fiber optic filaments 24 directs light uniformly into the skin of the patient around the lesion that is centrally positioned inside the ring light source. The light from the ring light source is directed into the skin so as to create in the skin around the lesion a conical converging ring of light. As shown in FIG. 3, this converging conical ring of light creates a point of light below the lesion where the ring of light converges to a point. Achieving this point of light provides uniform illumination of the above lesion via transillumination from within the skin of the patient. As a result of this uniform transillumination, accurate images of the lesion are obtained in the plurality of mirrors.

Figure 2:
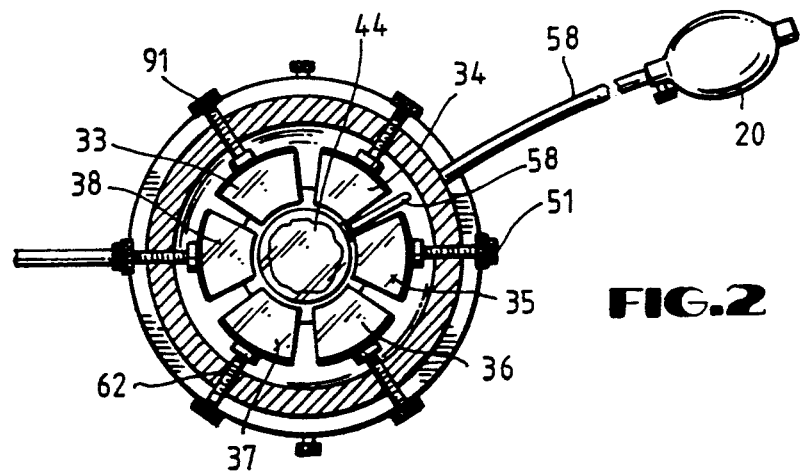
FIG. 2 is a cross-sectional top view of the nevoscope taken along line 2—2 of FIG. 1.

Referring now to FIG. 2, the mirror housing 32 contains six mirrors 33-38 which are mounted on pivotable arms 40 as shown in FIGS. 1 and 3. The lower section of each mirror is attached to a spring loaded telescopic arm 43, horizontally mounted in spring chamber 42 as shown in FIG. 3, thus providing a means for adjusting the angle of the mirror. There is a one-to-one correspondence between the number of spring chambers and the number of mirrors in the mirror housing. Each spring chamber is mounted on the inner wall of the mirror housing at a position radially outward from the lower central portion of a mirror.

The spring in spring chamber 42 pushes telescopic arm 43 toward the mirror 34 thereby tending to rotate mirror 34 clockwise about pivot arm 40. Pivot arm 40 is mounted between the inner wall of the mirror housing 32 and the central portion of mirror 34. The clockwise rotation is limited by the position of stop arm 62. Stop arm 62 extends from outside the mirror housing 32, through the wall of the mirror housing 32 and radially inward to the top edge of mirror 34. The radial penetration of stop arm 62 into mirror housing 32 can be adjusted by rotating the thumbwheel 91 on the outer end of stop arm 62. Thus, by adjusting the radial penetration of stop arm 62, the angle of mirror 34 can be adjusted. The above discussion regarding mirror positioning is applicable to each of mirrors 33-38.

A block diagram of a preferred method used to detect, analyze and diagnose a skin lesion is shown in FIG. 5. A picture of the skin lesion is taken using a camera 74 coupled to an optical transilluminating device 72, i.e., the nevoscope of the invention. The camera is then fitted with a color filter 8, as shown in FIG. 1, and color component images of the skin lesion are taken. The skin lesion images are then digitized using a conventional digitizing means 76 well known in the art, such as Micro-Imager TM by Servidyne Systems, Inc.

The digitized images are process for such attributes as texture and color by an image processor 78. A computer-based image processor can be employed in this application.

In a preferred embodiment, the nevoscope of the invention employs sufficient mirrors to cover the entire circumference of a lesion. A picture of an object taken with N mirrors will produce N+1 images. These N+1 images makeup a frame comprised of one direct view image of the skin lesion and N mirror images of the skin lesion.

In the present invention, the N mirror images of the skin lesion present views of the lesion which surround the direct view image of the lesion. The edges of the mirrors are also visible in the N mirror images of the skin lesion.

The N+1 images produced by the nevoscope having N mirrors are recorded by a camera 74 and then digitized by digitizer 76. The N+1 digitized images are then stored in a computer memory. The multiple images appearing in the digitized frame are separated and then positioned in a common orientation. Orientation of the mirror images is accomplished by extracting each mirror image in a particular frame and orienting the mirror image such that the mirror edge appears in the vertical dimension. The N mirror images are then lined up with the center image such that the center points of all N+1 images lie along the same horizontal line.

The oriented multiple views are aligned along their respective sectional planes. The projection along each sectional plane is then determined by measuring the gray scale values along each sectional plane.

A three-dimensional digital image of the skin lesion is reconstructed from the computed projections along each vertical sectional plane using equation (7) as explained above. This digital three-dimensional image is then processed and analyzed to determine the lesion boundary using the boundary determination algorithm of this invention.

The boundary determination algorithm requires the skin lesion analyst to visually examine the digital image and select a subimage lying entirely within the skin lesion as well as a subimage lying entirely outside the skin lesion, known as the background. The gray scale values of the pixels appearing in each of these subimages are measured to produce a histogram for each subimage. The gray scale range for each skin lesion subimage is determined from the skin lesion histogram.

The digital image is visually examined to estimate which pixels lie on the skin lesion/background boundary and a list of these initial skin lesion/background boundary pixels is made. One of these pixels is then selected for analysis using the boundary determination algorithm.

The gray scale values of eight pixels which are contiguous to the selected pixel are measured. Each measured gray scale value is compared with the previously measured skin lesion gray scale range. The percentage of pixel gray scale values that fall within the skin lesion gray scale range, known as Y, is computed. A minimum acceptable expansion pass rate, known as X, is also selected. In a preferred embodiment, X is equal to 70 percent. In the event that Y is greater than X, the listed boundary pixel is assigned to the skin lesion. A new skin lesion gray scale range is then recomputed, taking into account the gray scale value of the added pixel. Each listed boundary pixel where Y is less than X is assigned to the background.

The preceding steps are then repeated for the pixels that are contiguous to the pixel array which was just measured. In mathematical terms where the listed pixel array is (N×N) pixels, the expanded pixel array is (N+2)×(N+2) pixels. Each time the pixel array is expanded, as expressed above, the number of new pixels whose gray scale values are measured is (4N+4).

This array expansion process is continued until Y is less than X. At this point, the next listed pixel from the initial list of skin lesion/background pixels, which has not already been assigned to the skin lesion or the background, is selected and analyzed as set forth above. This process is repeated until all pixels in the initial list of skin lesion/background boundary pixels have been assigned to either the skin lesion or the background.

The size and thickness of the skin lesion are computed from the reconstructed cross-sections by measuring the number of pixels encompassed by the lesion and multiplying that number by the pixel scale dimension. The pixel scale dimension is computed by comparing the actual spatial distance between the mirrors with the number of pixels in the digitized frame separating the edges of the mirrors.

The present invention may make use of color component images taken with blue, green, and red filters in order to analyze the color and texture characteristics of the skin lesion. In this instance, the brightness level of each pixel in each of the tree color component images is measured. Each pixel is then given a composite brightness value, based upon the brightness values in each of its color component images. A spectrum histogram is then computed from these brightness values.

The pigmentation pattern of a skin lesion is determined from gray scale data for the digitized image. The first order histogram, $H(Y_i,d)$, is also computed. This histogram measures the frequency difference of gray scale values, $Y_i$, occurring along an image axis. Measurements taken along the axis are separated by a distance, d. A second order histogram, $H(Y_i,Y_j,d)$, is also computed. This histogram measures the frequency of occurrence of particular pairs of gray scale values, $Y_i$ and $Y_j$, that are separated along an image axis by a distance, d. The first order and second order histograms are then analyzed in order to locate their peaks. The entropy, E, is calculated from the histogram data, using the following equation:

$$E = - \sum_{y_i} \sum_{y_j} H(y_i,y_j,d) \ln H(y_i,y_j,d) \quad (8)$$

The undated measure, IM, is computed using the following formula:

$$IM = \sum_{y_i} \sum_{y_j} (Y_i - Y_j)^2 H(y_i,y_j,d) \quad (9)$$

The mean, M, the variance, V, and the standard deviation, SD, are calculated using the following formulas:

$$M = \frac{1}{N} \sum_{i=1}^{N} y_i \quad (10)$$

$$V = \frac{1}{N} \sum_{i=1}^{N} (y_i - M)^2 \quad (11)$$

$$SD = (V)^{\frac{1}{2}} \quad (12)$$

where N is the total number of points, $Y_i$, measured. Analogous formulas are used to calculate the mean, variance, and standard deviation of points, $Y_j$. The degree of correlation, C, is then computed using the following equation:

$$C = \frac{1}{SD(y_i)SD(y_j)} \sum_{y_i} \sum_{y_j} (y_i - y_j')(y_j - y_j')H(y_i,y_j,d) \quad (13)$$

Where SD(x) denotes the standard deviation of variable x, and x' denotes the mean of variable x.

The data relating to the histogram peaks, entropy, inertia measure, correlation, and Fourier spectrum may be stored in a knowledge-based system. This data may then be analyzed to determine the skin lesion pigmentation pattern.

The size, thickness, boundary, color, texture, and pigmentation of a skin lesion are preferably stored in a knowledge-based system and analyzed to diagnose the skin lesion such as in diagnostic expert system 80 of FIG. 5. The results of this diagnosis may be analyzed using other probabilistic models contained in a knowledge-based system to obtain a prognosis of the skin lesion such as in prognostic expert systems 82.

Many modifications and variations may be made in the embodiments described herein and depicted in the accompanying drawings without departing from the concept of the present invention. Accordingly, it is clearly understood that the

What is claimed is:

1. An apparatus for observing nevi, lesions, or other abnormalities in the skin, said apparatus comprising:
   (a) means for receiving a specimen of skin containing said abnormality of interest;
   (b) means for transilluminating the specimen of skin, said means for transilluminating includes means for uniformly directing light into the skin surrounding said abnormality in the shape of a converging ring of light having a focal point in the skin of the patient below said abnormality,
   (c) vacuum means coupled to said specimen receiving means for creating a vacuum contact between said transillumination means and skin surrounding said abnormality to facilitate the coupling of said ring of light into the skin of the patient;
   (d) means for recording multiple mirror images of the transilluminated abnormality; and
   (e) means for generating a three-dimensional reconstruction of said abnormality from said multiple mirror images.

2. A portable nevoscope for examining in situ a skin lesion of a patient, comprising:
   (a) a transparent, cup-like specimen housing having a central axis and a base with a central aperture for receiving a specimen of skin of a patient, said specimen of skin containing said lesion to be examined;
   (b) a transillumination means for transilluminating said specimen surrounding said specimen housing and for transmitting light in a converging ring of light into the skin of the patient around lesion to form a point of light at a point below said lesion thereby to uniformly transilluminate said lesion from within the skin of the patient;
   (c) a means for establishing a vacuum in said cup-like specimen housing to facilitate coupling between said transillumination means and the skin of the patient surrounding said lesion;
   (d) a mirror housing positioned around said specimen housing, said mirror housing containing a plurality of mirrors positioned for viewing mirror images of said lesion in said specimen housing each mirror having a tilt angle, said mirror housing being rotatable about said central axis to provide multiple positions for viewing images of said lesion, each mirror having a means for adjusting the tilt angle of said mirror with respect to said central axis to allow each mirror to be tilted thereby to obtain at any position of said mirror housing images at different angles of a portion of said lesion; and
   (e) a lens housing coupled with said mirror housing, said lens housing having a lens and an eyepiece for viewing said mirror images of said specimen of skin within said specimen housing, said rotatable mirror housing and said rotatable mirrors enabling said nevoscope to obtain multiple images of said lesion.

3. The nevoscope of claim 2 wherein the lens provides a depth of focus sufficient to focus all images seen through the nevoscope.

4. The nevoscope of claim 2 wherein said mirror tilt adjusting means comprises:
   (a) a plurality of spring chambers mounted on an inner wall of said mirror housing, each of said spring chambers mounted at a position radially outward from a lower central portion of one of said mirrors;
   (b) a plurality of telescopic arms, each of said telescopic arms horizontally mounted in one of said spring chambers and attached to one of said mirrors;

(c) a plurality of pivot arms, each of said pivot arms mounted between the inner wall of said mirror housing and a central portion of one of said mirrors; and (d) a plurality of adjustable arms, each of said stop arms extending through the inner wall of said mirror housing radially inward to a top edge of one of said mirrors, each said adjustable stop arm cooperating with an associated said telescopic arm to permit the tilt angle of the associated mirror to be adjusted.

5. The nevoscope of claim 2 further comprising:
(a) an entrance pupil mounted in the lens housing between the lens and the cup-like specimen housing.

6. The nevoscope of claim 2 further comprising a light source mounted in a wall of said lens housing at an angle to provide surface illumination of the specimen of skin in said cup-like specimen housing.

7. The nevoscope of claim 2 wherein the means for establishing a vacuum is a suction device inserted into said specimen housing.

8. The nevoscope of claim 7 wherein said suction device is an inlet tube having a first end inserted into said cup-like specimen housing and a second end attached to a squeeze bulb.

9. The nevoscope of claim 2 wherein said transillumination means comprises:
(a) an illuminator ring positioned around said cup-like specimen housing; and
(b) a plurality of fiber optic filaments uniformly dispersed in said illuminator ring and positioned to direct light onto the skin of the patient surrounding said lesion.

10. The nevoscope of claim 9 wherein said fiber optic filaments are directed downward at a 45° angle.

11. The nevoscope of claim 2 further comprising a camera mounted to said eyepiece wherein said camera can receive images through said eyepiece.

12. The nevoscope of claim 11 further comprising a digitizer electronically coupled to said camera.

13. The nevoscope of claim 12 further comprising an image processor coupled to said digitizer.

14. A portable nevoscope comprising:
(a) a lens housing having an upper end and lower end, said lens housing containing an eyepiece cylinder mounted in the upper end;
(b) a lens mounted in an axial position in said lens housing;
(c) a mirror housing having an upper end and a lower end, the upper end of said mirror housing being mechanically coupled with the lower end of said lens housing, said mirror housing further having a central axis;
(d) a plurality of mirrors spaced apart and mounted within said mirror housing near a wall of said mirror housing, each of said plurality of mirrors oriented to reflect toward said central axis of said mirror housing, each of aid mirrors including a means for tilting the mirror with respect to said central axis;
(e) a transparent cup-like specimen housing with a central aperture foe receiving a specimen of skin containing a skin lesion to be examined, said specimen housing centrally positioned in the lower end of said mirror housing, said mirror housing being rotatable with respect to said specimen housing to permit said mirrors to be rotated to multiple positions around said lesion for obtaining multiple images of said lesion, said specimen housing having a top and a base;
(f) an extension tube having an inner end and an outer end, the inner end of said extension tube extending into said specimen housing and the outer end of said extension tube extending out of said mirror housing;
(g) a means attached to the outer end of said extension tube for pulling a vacuum in said specimen housing;
(h) an illuminator ring positioned around the lower end of said mirror housing, said vacuum pulling means obtaining uniform contact between said illuminator ring and the skin of the patient surrounding said lesion to facilitate coupling of light into the skin of the patient; and
(i) a plurality of fiber optic filaments uniformly dispersed in said illuminator ring and positioned to direct light into the skin of the patient surrounding said lesion, said illuminator ring transmitting a converging ring of light into the skin of a patient to form a point of light at a point below said lesion thereby to uniformly transilluminate said lesion from within the skin of the patient.

15. The nevoscope of claim 14 wherein the axial position of said lens within said lens housing is adjustable.

16. The nevoscope of claim 14 further comprising a light source adjustably mounted in the lower end of said lens housing such that orientation of said light source can be varied.

17. The nevoscope of claim 14 further comprising:
(a) an entrance pupil mounted in said lens housing below said lens; and
(b) a focus correcting plate mounted in the upper end of said mirror housing.

18. The nevoscope of claim 17 further comprising:
(a) a camera mounted above said eyepiece cylinder wherein said camera can receive images through said eyepiece;
(b) a digitizer electronically coupled to said camera; and
(c) an image processor electronically coupled to said digitizer.

19. An in situ method of examining a nevi in the skin which comprises the steps of:
(a) isolating a specimen of skin which includes the nevi;
(b) uniformly transilluminating the nevi and the skin surrounding said nevi with a converging ring of light so as to form a point of light at a point below said nevi thereby to uniformly transilluminate said nevi from within the skin;
(c) recording images of the transilluminated nevi from a direct image and from reflected mirror images obtained at a plurality of angles at positions around said nevi; and
(d) generating a three-dimensional reconstruction of said nevi by computerized tomography from the recorded images thereby to obtain depth information of the nevi.

20. The method of claim 19, including the step of applying suction to the specimen of skin to provide uniform coupling of said ring of light into the skin surrounding said nevi.

21. A method for analyzing a skin lesion comprising the steps of:
(a) uniformly transilluminating the skin of the patient surrounding said lesion with a converging ring of light so as to form a point source of light at a point below said lesion thereby to uniformly transillumintate said lesion from within the skin of the patient;
(b) obtaining multiple images from adjustable mirrors reflecting respective two dimensional vertical sectional planes of the transilluminated skin lesion viewing range around the lesion, said adjustable mirrors permitting multiple images to be obtained of said lesion at different angles for a given position of said mirrors with respect to said lesion;
(c) digitizing each of said multiple images of said skin lesion to obtain a digitized image of said skin lesion;
(d) repeating steps (a) through (c) with a color filter to obtain color component images;
(e) separating the multiple images of said skin lesion appearing in said digitized image;
(f) placing each of said multiple images in a common orientation;
(g) aligning said oriented multiple images along said respective two-dimensional vertical sectional planes;
(h) computing one-dimensional projections from each aligned image along each of said vertical two-dimensional sectional planes; and
(i) computing two-dimensional vertical cross-sectional reconstructions from the computed one-dimensional projections for each of said two-dimensional vertical sectional planes to obtain a three-dimensional reconstruction of the skin lesion.

22. The method of claim 21 wherein said color filter is green.

23. The method of claim 21 wherein said color filter is red.

24. The method of claim 21 wherein said color filter is blue.

25. The method of claim 21 further comprising the steps of:
(a) computing a thickness of said skin lesion; and
(b) computing a size of said skin lesion.

26. The method of claim 21 further comprising the steps of analyzing the color and texture characteristics of said color component images wherein said step of analyzing comprises the steps of:
(a) measuring a brightness level of each pixel in each of said color component images; and
(b) computing a spectrum histogram from said brightness levels.

27. The method of claim 21 further comprising the step of detecting a boundary of said skin lesion.

28. The method of claim 27 wherein the step of detecting the boundary of said skin lesion comprises the steps of:
(a) selecting a subimage lying entirely within said skin lesion from said digitized image;
(b) selecting a subimage lying entirely with a background from said digitized image;
(c) computing a histogram of said skin lesion subimage;
(d) computing a histogram of said background subimage;
(e) selecting a skin lesion gray scale range from said histogram of said skin lesion subimage;
(f) listing pixel coordinates of boundary pixels located near a boundary of the skin lesion subimage and the background subimage;
(g) selecting a minimum acceptable expansion pass rage, known as X;
(h) recording the gray scale values for a pixel array comprising each pixel that is contiguous to said boundary pixels;
(i) computing a percentage of pixel gray scale values recorded in step (h) that fall within said skin lesion gray scale range, said percentage to be known as Y;
(j) assigning each of said boundary pixels where Y is greater than X to said skin lesion;
(k) recomputing said skin lesion gray scale range;
(l) assigning each of said boundary pixels where Y is less than X to said background;
(m) redefining said boundary pixels to include only pixels where Y is greater than X;
(n) recording the gray scale values for a pixel array comprising each pixel that is contiguous to said boundary pixels;
(o) computing a percentage of pixel gray scale values recorded in step (n) that fall within said recomputed skin lesion gray scale range, said percentage to be known as Y;
(p) assigning each of said boundary pixels where Y is greater than X to said skin lesion;
(q) recomputing said skin lesion gray scale range;
(r) assigning each of said boundary pixels where Y is less than X to said background; and
(s) repeating steps (m) through (r) until no more boundary pixels exist where Y is greater than X.

29. The method of claim 27 wherein the step of detecting the boundary of said skin lesion comprises the steps of:
(a) visually approximating a location of the skin lesion boundary;
(b) computing a gray scale range of a subimage lying entirely within said skin lesion;
(c) computing a gray scale range of a subimage lying entirely with a background;
(d) computing a gray scale of an image region lying contiguous to a portion of the visually approximated skin lesion boundary;
(e) comparing the gray scale range for said image region with the gray scale range of each of said subimages;
(f) computing the location of the skin lesion boundary in a vicinity of said image region, based upon said comparison; and
(g) repeating steps (b) through (f) until an entire skin lesion boundary has been computed.

30. The method of claim 21 further comprising the step of computing a pigmentation pattern of said skin lesion.

31. The method of claim 30 wherein the steps of computing the pigmentation pattern of said skin lesion comprises:
(a) computing a first order histogram, denoted by $H(y_i, d)$;
(b) computing a second order histogram, denoted by $H(y_i, y_j, d)$;
(c) analyzing said first order histogram to find peaks;
(d) analyzing the second order histogram to determine peaks;
(e) computing a histogram entropy, denoted by E, where:

$$E = - \sum_{y_i} \sum_{y_j} H(y_i,y_j,d) \ln H(y_i,y_j,d);$$

(f) computing a histogram inertia measure, denoted by IM, where:

$$IM = \sum_{y_i} \sum_{y_j} (y_i - y_j)^2 H(y_i,y_j,d);$$

(g) computing a degree of correlation, denoted by C, where:

$$C = \frac{1}{SD(y_i)(SD)(y_j)} \sum_{y_i} \sum_{y_j} (y_i - y_j')(y_j - y_j') H(y_i,y_j,d)$$

(h) inputting data computed on steps (c) through (g) above, into a knowledge-based system containing skin lesion probabilistic models; and (i) analyzing data stored in said knowledge-based system to determine the skin lesion pigmentation pattern.

32. The method of claim 30 further comprising the steps of:
 (a) storing computed skin lesion characteristics in a knowledge-based system; and
 (b) analyzing the skin lesion characteristics stored in said knowledge-based system to obtain a skin lesion diagnosis.

33. The method of claim 32 further comprising the steps of:
 (a) storing the skin lesion characteristics in a knowledge-based system containing skin lesion prognostic probabilistic models; and
 (b) analyzing the skin lesion characteristics stored in said knowledge-based system to obtain a prognosis of the skin lesion.

* * * * *

UNITED STATES PATENT AND TRADEMARK OFFICE
CERTIFICATE OF CORRECTION

PATENT NO. : 5,146,923
DATED : September 15, 1992
INVENTOR(S) : Atam P. Dhawan

It is certified that error appears in the above-identified patent and that said Letters Patent are hereby corrected as shown below:

Claim 1, column 12, line 11, delete [,] and insert therefor

--;--.

Claim 2, column 12, line 31, after the word "around" and before the word "lesion" insert the word --said--.

Claim 4, column 13, line 7, after the word "adjustable" and before the word "arms" insert the word --stop--.

Claim 14, column 13, line 50, after "(b", insert a --)--.

Claim 14, column 13, line 61, delete [aid] and insert therefore --said--.

Claim 14, column 13, line 65, delete [foe] and insert therefor

--for--.

Claim 21, line 5, delete [source].

Claim 28, column 15, line 61, delete the word [with] and insert therefor --within--.

UNITED STATES PATENT AND TRADEMARK OFFICE
CERTIFICATE OF CORRECTION

PATENT NO. : 5,146,923
DATED : September 15, 1992
INVENTOR(S) : Atam P. Dhawan

It is certified that error appears in the above-identified patent and that said Letters Patent are hereby corrected as shown below:

Claim 28, column 16, line 5, delete the word [rage] and insert therefor --rate--.

Claim 31, column 17, line 3, in the formula delete [-] which comes after the = sign.

Claim 32, column 18, line 9, delete the word [a].

Signed and Sealed this

Twenty-eighth Day of September, 1993

Attest:

BRUCE LEHMAN

Attesting Officer

Commissioner of Patents and Trademarks